(12) United States Patent
Kuhn

(10) Patent No.: US 8,781,547 B2
(45) Date of Patent: Jul. 15, 2014

(54) METHOD AND APPARATUS FOR CALIBRATING AN ABSOLUTE OXYGEN SATURATION SENSOR

(75) Inventor: Jonathan L. Kuhn, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 251 days.

(21) Appl. No.: 13/283,930

(22) Filed: Oct. 28, 2011

(65) Prior Publication Data

US 2013/0109938 A1    May 2, 2013

(51) Int. Cl.
    *A61B 5/1455*    (2006.01)
(52) U.S. Cl.
    USPC ............................ 600/331; 600/323; 600/341
(58) Field of Classification Search
    USPC ......... 600/310, 316, 322, 323, 324, 326, 328, 600/331, 333, 336, 341, 473, 476; 356/41
    See application file for complete search history.

(56) References Cited

U.S. PATENT DOCUMENTS

| | | | |
|---|---|---|---|
| 4,230,122 A | 10/1980 | Lubbers et al. | |
| 5,638,816 A * | 6/1997 | Kiani-Azarbayjany et al. | 600/316 |
| 5,879,294 A | 3/1999 | Anderson et al. | |
| 5,902,326 A | 5/1999 | Lessar et al. | |
| 6,377,840 B1 | 4/2002 | Gritsenko et al. | |
| 6,473,632 B1 | 10/2002 | Myers | |
| 6,481,899 B1 | 11/2002 | Quast et al. | |
| 6,487,343 B1 | 11/2002 | Lewandowski et al. | |
| 6,599,250 B2 | 7/2003 | Webb et al. | |
| 6,615,064 B1 | 9/2003 | Aldrich | |
| 6,667,803 B1 | 12/2003 | Flessland et al. | |
| 6,682,135 B2 | 1/2004 | Zheng | |
| 6,839,583 B1 | 1/2005 | Lewandowski et al. | |
| 6,892,006 B2 | 5/2005 | Lewandowski et al. | |
| 7,043,294 B1 | 5/2006 | Paris | |
| 7,165,893 B2 | 1/2007 | Schmitz | |

(Continued)

FOREIGN PATENT DOCUMENTS

WO    2004091719    10/2004

OTHER PUBLICATIONS (PCT/US2012/049817) PCT Notification of Transmittal of the International Search Report and the Written Opinion of the International Searching Authority, Mailed Nov. 23, 2012, 12 pages.

(Continued)

*Primary Examiner* — Tse Chen
*Assistant Examiner* — Chu Chuan (J J) Liu
(74) *Attorney, Agent, or Firm* — Evans M. Mburu; Stephen W. Bauer

(57) ABSTRACT

A method for using a medical device comprising an optical sensor to measure calibrated oxygen saturation in a body tissue uses a standard spectral response of blood established for multiple of oxygen saturations and a standard spectral response of a reference material. The standard responses are established using a spectrometer. The spectral power output of the optical sensor is measured using a spectrometer. The optical sensor output signal response to the reference material is obtained. A processor computes a device-specific calibration curve for the medical device using the measured spectral power output and the standard spectral response of blood and computes an optical gain using the standard spectral response of the reference material and the measured spectral power output of the optical sensor. The device-specific calibration curve and optical gain of the optical sensor are stored in a memory of the medical device.

23 Claims, 8 Drawing Sheets

(56) References Cited

U.S. PATENT DOCUMENTS

| | | |
|---|---|---|
| 7,239,385 B2 | 7/2007 | Schmitz et al. |
| 7,239,901 B2 | 7/2007 | Gritsenko |
| 7,302,294 B2 | 11/2007 | Kamath et al. |
| 2005/0124870 A1* | 6/2005 | Lipson .................. 600/316 |
| 2007/0239052 A1 | 10/2007 | Bhunia |
| 2007/0239053 A1 | 10/2007 | Bhunia |
| 2007/0239215 A1 | 10/2007 | Bhunia et al. |
| 2007/0255148 A1 | 11/2007 | Bhunia |
| 2008/0004513 A1 | 1/2008 | Walker et al. |
| 2008/0208269 A1 | 8/2008 | Cinbis et al. |
| 2008/0306390 A1 | 12/2008 | Cinbis |
| 2010/0185262 A1 | 7/2010 | Kuhn |
| 2010/0317942 A1 | 12/2010 | Cinbis et al. |
| 2011/0196211 A1* | 8/2011 | Al-Ali et al. .................. 600/300 |

OTHER PUBLICATIONS

Dean E. Myers, Noninvasive method for measuring local hemoglobin oxygen saturation in tissue using wide gap second derivative near-infrared spectroscopy, Journal of Biomedical Optics 10(3), 034017 (May/Jun. 2005).

David A. Benaron, Quantitative Clinical Non-Pulsatile and Localized Visible Light Oximeter: Design of the T-Stat (Trade Marked) Tissue Oximeter, Stanford University School of Medicine, Palo Alto, CA USA 94305.

* cited by examiner

METHOD AND APPARATUS FOR CALIBRATING AN ABSOLUTE OXYGEN SATURATION SENSOR

FIELD OF THE DISCLOSURE

The disclosure relates generally to medical devices and, in particular, to an apparatus and method for calibrating an optical sensor included in a medical device for measuring absolute oxygen saturation (StO2).

BACKGROUND

Optical sensors have been proposed or implemented in medical devices for monitoring changes in blood or tissue oxygen concentration. When short-term, relative changes in oxygen concentration are monitored, calibration of the optical sensor is not necessarily required. For example, two-wavelength optical sensors can be used to detect relative changes in blood oxygen saturation over short intervals of time, e.g. less than one minute, without requiring calibration using oxygenated blood. However, determining absolute StO2 is desirable in many monitoring applications because absolute measurements allow changes in oxygen that occur over longer time intervals to be measured and compared and provides a better indication of the actual patient's oxygenation status at a given time.

Four wavelength optical sensors have been implemented in external monitoring devices, which allow absolute StO2 to be measured. Tightly controlled manufacturing specifications with narrow tolerances enable calibration of the external optical sensors to be performed by calibrating one device and applying the calibration results to all devices. The calibration procedure typically requires calibration using blood flowing in a loop and oxygenated at different saturation levels to obtain a calibration curve.

Maintaining stringent manufacturing specifications to enable a single calibration to be applicable to all devices, however, can add to the cost of manufacturing and the frequency of device rejection. Widening the tolerances of manufacturing specifications can reduce manufacturing costs with the trade-off that a single calibration curve may no longer be applicable to all sensing devices. Calibration of each individual device using a blood flow loop, however, would also add undue manufacturing cost and time burden. A need exists, therefore, for an optical sensing device and associated methods for monitoring absolute StO2 that does not require calibration of all individual sensing devices using a blood loop but still enables manufacturing without highly restrictive tolerances or complex components.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
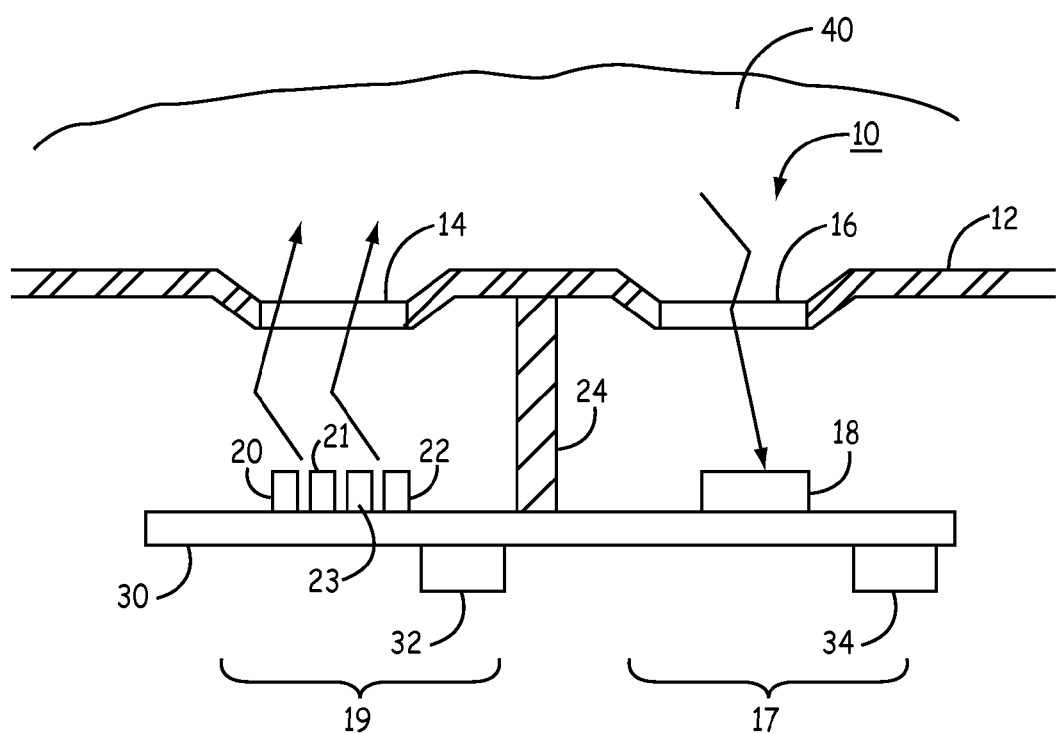
FIG. 1 is a partial sectional view of an optical sensor which may be implemented in a device configured to monitor absolute StO2.

FIG. 1 is a partial sectional view of an optical sensor 10 which may be implemented in a device configured to monitor absolute StO2. Sensor 10 includes a light detecting portion 17 and a light emitting portion 19. Sensor 10 is shown to include four light sources 20, 21, 22, and 23 and one light detector 18 mounted within a housing 12 of sensor 10. Methods and associated apparatus are described herein for calibrating sensor 10 to enable measurement of absolute StO2. These methods may be used in conjunction with other optical sensors that have different light emission and detection configurations than the illustrative example shown.

Other sensor configurations may include fewer or more light sources and light detectors than shown in FIG. 1. For example, a light source included in optical sensor 10 may be a single light source emitting white light. One or more light sources with optional filtering may be implemented for emitting selected light wavelengths or a narrowband spectrum of wavelengths from emitting portion 19. The emitted light includes desired wavelength(s) at which light attenuation by the adjacent body tissue or fluid 40 is to be measured. Any number of light sources may therefore be included in a light emitting portion 19 of sensor 10, and the methods described herein may be adapted for a corresponding number of light sources, i.e. number of light wavelengths for which attenuation spectra are being measured.

Illustrative embodiments described herein relate primarily to an optical sensor used in blood and tissue oximetry applications. The methods described, however, may be practiced in conjunction with any optical sensing application, and are not limited to particular wavelengths of emitted and measured light. In other applications, other light wavelengths or combinations of wavelengths may be measured to determine attenuation of light corresponding to a chromophore or metabolite of interest in a targeted body tissue or fluid for monitoring a patient condition. As will be described herein, a standard blood/tissue spectral response and a standard reference material spectral response are obtained to provide standardized remittance curves for use in calibrating multiple devices. In other embodiments that are not measuring oxygen saturation of the blood or tissue, a different suitable body tissue or fluid and a suitable reference material or tissue phantom could be substituted for oxygenated blood and a blood/tissue phantom for use in the calibration methods described herein.

Light sources 20 through 23 are mounted on one side of a sensor hybrid circuit board 30 in light emitting portion 19 of sensor 10. Light sources 20 through 23 are electrically coupled to integrated circuitry 32 for delivering appropriately-timed drive signals to the light sources for controlling the intensity, frequency and time intervals of emitted light. When more than one light source is included in emitting portion 19, light may be emitted sequentially in a time-multiplexed manner or simultaneously in a frequency multiplexed manner.

Emitted light passes through lens 14 into an adjacent tissue volume 40, which may be a blood-perfused body tissue, a blood volume or other body fluid volume. As used herein, the term "tissue" includes body fluids such as blood. As such, volume 40 may be a volume of blood flowing through a blood vessel or a heart chamber. In other applications, volume 40 is a blood-perfused body tissue, such as muscle tissue, brain tissue, cardiac tissue, etc. being monitored by the optical sensor 10.

Light that is reflected or scattered by the tissue volume 40 is received by sensor 10 through lens 16 of light detecting portion 17. Sensor 10 is shown in a "reflection" configuration in that the emitting and detecting portions 19 and 17 are arranged in a side-by-side manner, along a common side of tissue volume 40, such that remitted light is reflected or scattered by tissue volume 40 back into light detecting portion 17. In an alternative embodiment, sensor 10 may be configured in a "transmission" configuration wherein the emitting and detecting portions 19 and 17 are arranged in facing opposition. The emitting and detecting portions 19 and 17 would be positioned on approximately opposite sides of the tissue volume 40 with tissue volume 40 positioned between the opposing emitting and detecting portions. In a transmission configuration, remitted light is light that is transmitted through the tissue volume 40. In either configuration, a measurement of remitted light by light detector 18 is correlated to the attenuation of emitted light.

Light detector 18 is mounted on hybrid circuit board 30, or alternatively a separate circuit board, in a light detecting portion 17 of sensor 10. Detector 18 is electrically coupled to integrated circuitry 34 for receiving current emitted by detector 18 and for transferring an analog or digital signal to signal processing circuitry included in an associated medical device. In various embodiments, one or more light detecting elements may be included in light detecting portion 17, which may be sensitive to a wide or narrow-band spectrum of light wavelengths according to the particular monitoring application.

Integrated circuits 32 and 34 are electrically coupled to conductors (not shown), which may extend through a medical lead body when sensor 10 is carried by an elongated medical lead used for intravascular or extra-vascular advancement to a desired StO2 monitoring site. In an alternative embodiment, sensor 10 is not carried along a lead and is incorporated in the housing of a medical device in which case integrated circuits 32 and 34 are electrically coupled to other medical device circuitry by conductors or wires within the medical device housing (which may correspond to sensor housing 12).

Sensor 10 includes light barrier or baffle 24 disposed between light emitting portion 19 and light detecting portion 17. Light barrier 24 prevents spurious detection of light by detecting portion 17 that is directly reflected or refracted from emitting portion 19 and not scattered or reflected by tissue volume 40 into light detecting portion 17. Lenses 14 and 16 are typically formed of a flat panel, cylinder or half-cylinder of glass, sapphire, ruby, quartz or any other suitable light transparent material. Light emitting portion 19 and light detecting portion 17 may each have a discrete lens 14 and 16, respectively. Alternatively, a single lens may be provided with light barrier 24 separating the light detecting and emitting portions 17 and 19, respectively.

In a four wavelength optical sensor, the attenuation of the four emitted wavelengths is used for computing a scaled second derivative (S2D) of the light attenuation spectra. Calibration coefficients are then used with the scaled second derivative to compute absolute StO2 as a function of S2D. The scaled second derivative method for computing StO2 is described in commonly-assigned U.S. patent application Ser. No. 12/771,322, hereby incorporated herein by reference in its entirety.

Light sources 20 through 23 are embodied as four light emitting diodes (LEDs) emitting light at separate wavelengths of 680 nm, 720 nm, 760 nm, and 800 nm in one example. Alternatively, four LEDs may emit light at 660 nm, 720 nm, 760 nm, and 810 nm. In another embodiment, four LEDs emit light at 720 nm, 760 nm, 810 nm, and 850 nm. In yet another embodiment, four LEDs are included that emit light at 720 nm, 760 nm, 810 nm, and 890 nm. Any combination of light sources emitting light at any of the wavelengths mentioned herein may be used. Furthermore, it is recognized that the specified wavelengths are approximate and each light source may emit a narrow band of light wavelengths which is approximately centered on, or at least includes, the specified wavelength. The light sources may be controlled to emit light sequentially or simultaneously.

The light sources 20 through 23, also referred to herein as light "emitters", and light sources in any of the sensor configurations described herein, may be embodied as a single white light source or multiple light sources emitting light at separate spaced-apart wavelengths as previously described. Suitable light sources include, without limitation, optoelectronic devices such as light emitting diodes (LEDs), lasers such as VCSELs, or luminescent, phosphorescent or incandescent light sources, or any combination thereof.

The light detector 18, and light detectors in any of the sensor embodiments described herein, may be embodied as a photodiode. Other components suitable for use as a light detector include a photoresistor, phototransistor, photovoltaic cell, photomultiplier tube, bolometer, charge-coupled device (CCD) or an LED reverse-biased to function as a photodiode.

The attenuation of the remitted light received by light detector 18 is measured at four center wavelengths in the scaled second derivative method. In the example of using measurements at 680 nm, 720 nm, 760 nm, and 800 nm, the second derivatives of the attenuation spectra at 720 nm and 760 nm are computed. The second derivative at 720 nm is scaled or normalized by the second derivative at 760 nm and used to obtain an absolute measurement of StO2 using previously established calibration coefficients and constants. The second derivative of light attenuation at 760 nm is dependent on the total hemoglobin concentration present in the tissue and the oxygenated state of the total hemoglobin present. This second derivative of the attenuation measured at 760 nm can therefore be used to compute a total hemoglobin concentration index (THI). The THI can also be a calibrated measurement as will be described herein.

Figure 2:
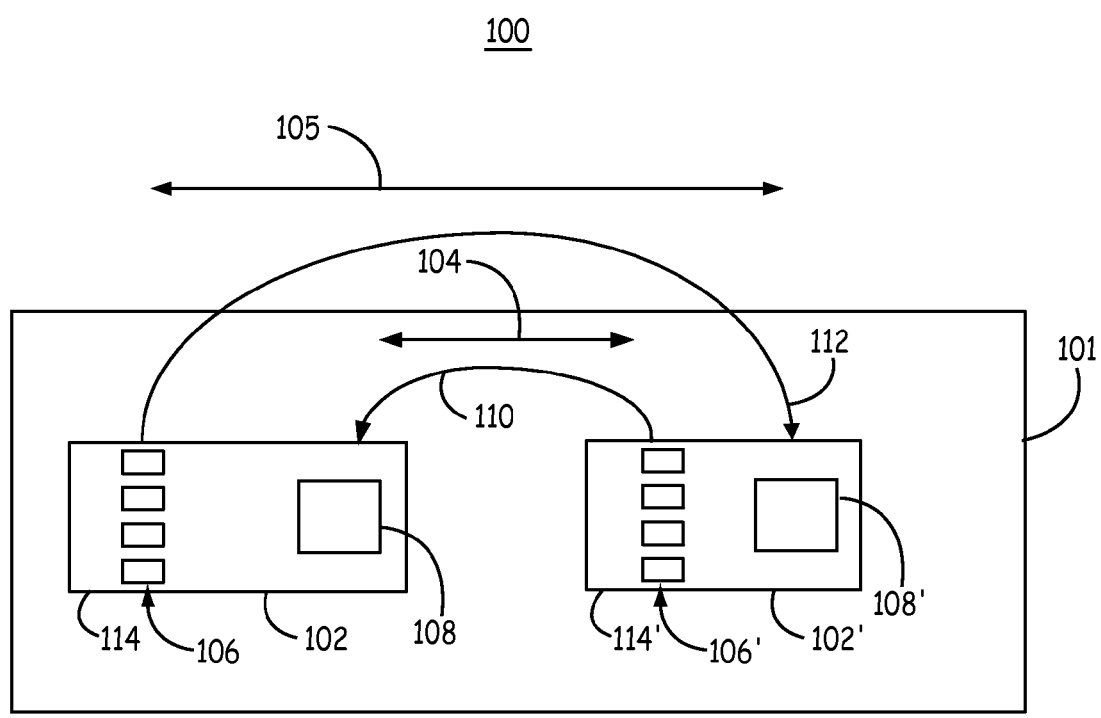
FIG. 2 is a top schematic view of an optical sensor according to an alternative embodiment.

FIG. 2 is a top schematic view of an optical sensor 100 according to an alternative embodiment. Sensor 100 includes two optical sensing units 102 and 102', which may be provided with substantially identical (within specification tolerances) light emitting and light detecting components that are co-located in the optical sensing units 102 and 102'. Specifically, units 102 and 102' each include respective light sources 106 and 106' emitting light through respective emitting windows 114 and 114' and light detectors 108 and 108' receiving light through respective windows 114 and 114'. Windows 114, 114' are formed in housing 101, which may correspond to a housing of a dedicated optical sensor or a medical device incorporating sensor 100 for StO2 monitoring but also performing other sensing and/or therapy delivery functions. The functionality of each sensing unit 102 and 102' may be selectable or programmable such that one unit emits light from light source 106 or 106' and the other unit detects light at light detector 108 or 108'. As such, each unit 102 and 102' will function as either an emitting portion or a detecting portion and that function is programmable or selectable. A light barrier between light sources 106, 106' and respective detector 108, 108' within unit 102, 102' is not necessary since each unit 102 and 102' will function either as an emitter or as a detector by selectively enabling only the light sources 106 or 106' or only the light detector 108 or 108' to operate at any given time within a given unit 102, 102'.

By arranging the light sources 106 and 106' and the light detectors 108 and 108' in a particular spatial manner with respect to one another, at least two different separation distances 104 and 105 exist between light sources 106' and detector 108 and between light sources 106 and detector 108', respectively. To illustrate, if sensing unit 102 is enabled to emit light, light detector 108 is disabled and light sources 106 are controlled to emit light according to a monitoring protocol. Remitted light is received by light detectors 108', which is enabled to provide a signal responsive to received light. Light sources 106' are disabled such that sensing unit 102' forms a light detecting portion of sensor 100. The distance 104 or 105 between the selected emitting and detecting portions of the sensor determines, in part, the optical pathway shown schematically by arrows 110 and 112, respectively, of the sensor 100 and thus determines the measurement volume and depth in the tissue of interest.

The sensing units 102 and 102' may be controlled to operate as emitting portions or detecting portions at different times during StO2 monitoring. This selective control of emitting and detecting functionality of co-located components allows measurements to be made in different tissue volumes. As described below, the power spectra of the light sources and the voltage signal from the light detector when the sensor is positioned against a reference material are measured for use in obtaining calibration constants for the sensor. When co-located emitting and detecting components are included in a sensor enabling more than one combination of emitting and detecting portions to be selected, calibration of both combinations may be performed. Alternatively, if the selection of emitting and detecting portions will be fixed during StO2 monitoring, calibration measurements may be performed only for the selected emitting and detecting combination.

Figure 3:
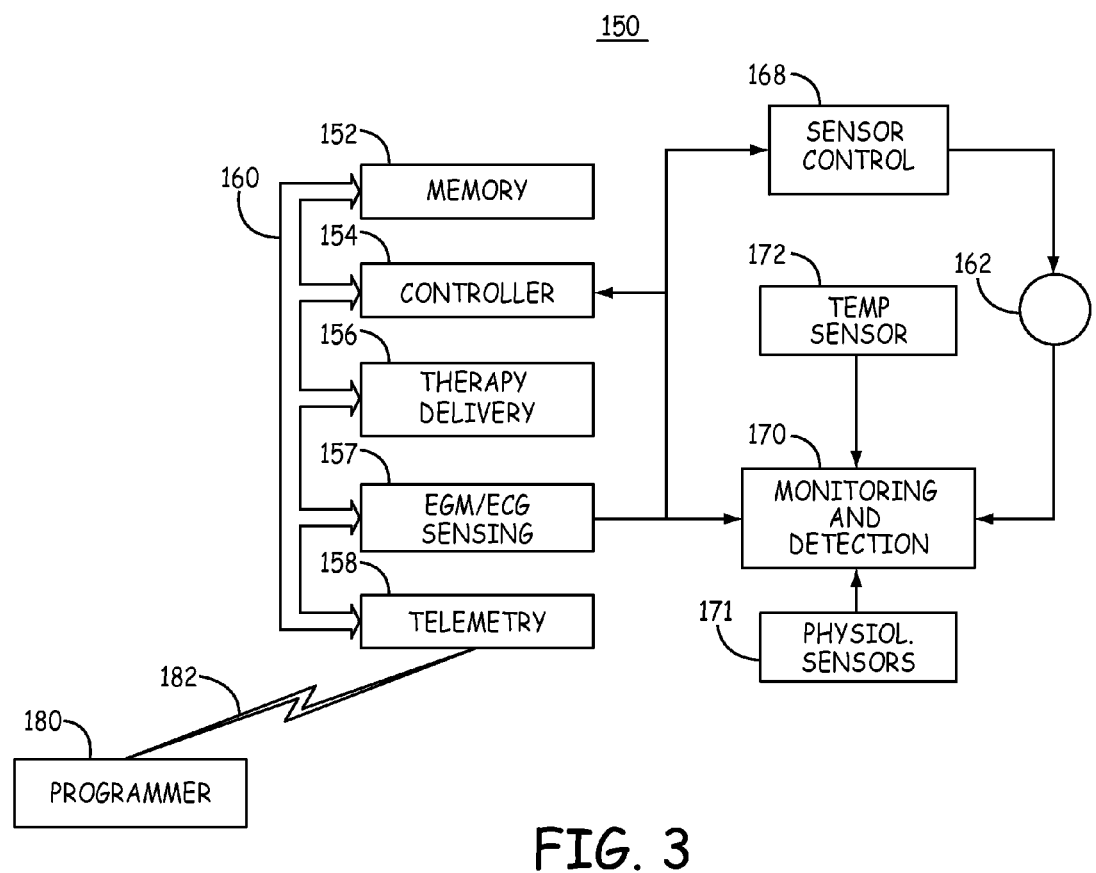
FIG. 3 is a functional block diagram of one implantable medical device (IMD) in which an optical sensor may be implemented and calibrated for measuring absolute StO2 according to the methods disclosed herein.

FIG. 3 is a functional block diagram of one embodiment of an implantable medical device (IMD) 150 in which an optical sensor may be implemented and calibrated for measuring absolute StO2 according to the methods disclosed herein. Examples of medical devices and systems that may incorporate an optical sensor for measuring absolute StO2 for patient monitoring and/or therapy control are generally disclosed in commonly assigned U.S. Patent Publication No. 2007/0255148 (Bhunia), U.S. Patent Publication No. 2008/0306390 (Cinbis) and U.S. Pat. No. 6,599,250 (Webb et al.), all of which are hereby incorporated herein by reference in their entirety. It is understood that an optical sensor for measuring absolute StO2 may be implemented in conjunction with numerous types of internal or external patient monitoring or therapy delivery devices. Such devices may include monitoring only devices used to detect a patient condition and provide a warning or alert or generate diagnostic or prognostic data. For example, an external optical sensor may be provided for ambulatory or bedside monitoring of tissue StO2. In other embodiments, an implantable medical device may be provided with an optical sensor for monitoring StO2, for example in association with hemodynamic monitoring. An IMD may be a monitoring-only device or may be capable of delivering a therapy, such as cardiac pacing and/or cardioversion and defibrillation, neurostimulation, or drug delivery.

IMD 150 is embodied as an implantable cardiovertor defibrillator (ICD) in one embodiment, including an EGM/ECG sensing module 157 and therapy delivery module 156. IMD 150 includes memory 152, a controller 154, and a telemetry module 158. An optical sensor 162, which may correspond to sensor 10 or sensor 100 shown in respective FIGS. 1 and 2, is coupled to sensor control module 168 and a monitoring and detection module 170. Monitoring and detection module 170 may receive signals from EGM/ECG sensing module 157 and other physiological sensors 171 for detecting events or conditions and for use by controller 154 in determining a need for therapy. For example, monitoring and detection module 170 may use an StO2 signal, in combination with cardiac EGM or ECG signals, for detecting a hemodynamically unstable cardiac arrhythmia which requires a cardioversion or defibrillation shock.

Optical sensor 162 includes integrated circuitry for delivering appropriately-timed drive signals to light sources in an emitting portion of sensor 162 for controlling the intensity, frequency and time intervals of emitted light. Sensor control module 168 provides signals to sensor 162 to coordinate the beginning time, duration, and frequency of drive signals produced by circuitry in sensor 162. Drive signals may be applied to cause sequential light emission at different wavelengths or simultaneous, frequency multiplexed light emission. Sensor control module 168 may be programmed to cause sensor 162 to operate according to a monitoring protocol and/or may receive signals from controller 154 to control sensor 162 operation on a triggered or scheduled basis. Sensor 162 additionally includes integrated circuitry for receiving current emitted by the light detector included in the light detection portion of sensor 162 and for transferring an analog or digital signal to monitoring and detection module 170.

Monitoring and detection module 170 uses calibration coefficients stored in associated memory or in memory 152 for determining a calibrated measurement of StO2 and, in some embodiments, THI. The calibration coefficients may be programmed into memory 152 or memory included in monitoring and detection module 170 using a programmer 180 communicating with telemetry module 158 via telemetry link 182.

Because the light sensor voltage signal may be temperature dependent, IMD 150 includes a temperature sensor 172 for providing a temperature-correlated voltage signal to monitoring and detection module 170. Monitoring and detection module 170 determines a temperature-compensated optical gain of the light detector signal using the temperature sensor voltage signal as will be described in greater detail in conjunction with FIG. 9.

EGM/ECG sensing module 157 includes cardiac electrodes for use in sensing intracardiac or transvenous EGM signals or subcutaneous ECG signals for detecting and discriminating heart rhythms. IMD 150 may include other sensors included in sensor 171 for sensing physiological signals such as blood pressure, patient activity, patient posture, or the like. Such sensor signals may be used in combination with the monitored StO2 and THI by controller 154 for determining when a therapy is needed and delivered by therapy delivery module 156. Therapy delivery module 156 includes an electrical pulse generator for delivering cardiac pacing pulses and higher voltage cardioversion/defibrillation shocks. In other embodiments, a pulse generator is used for delivering neurostimulation pulses. Therapy delivery module 156 may additionally or alternatively include a fluid delivery pump for delivering a pharmaceutical or biological fluid to the patient.

Data acquired by controller 154 relating to StO2 and THI may be stored in memory 152 and/or transferred to an external programmer 180 via wireless telemetry module 158 for review by a clinician. Controller 154 transmits data to and from memory 152, therapy delivery module 156, EGM/ECG sensing module 157, and telemetry module 158 via data/address bus 160.

Memory 152 may include computer-readable instructions that, when executed by controller 154, cause IMD 150 and controller 154 to perform various functions attributed to IMD 150, controller 154, and monitoring and detection module 170. The computer-readable instructions may be encoded within memory 152. Memory 152 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Controller 154 may include any one or more of a microprocessor, a controller, a digital signal processor (DSP), an application specific integrated circuit (ASIC), a field-programmable gate array (FPGA), or equivalent discrete or integrated logic circuitry. In some examples, controller 154 may include multiple components, such as any combination of one or more microprocessors, one or more controllers, one or more DSPs, one or more ASICs, or one or more FPGAs, as well as other discrete or integrated logic circuitry. The functions attributed to controller 154 herein may be embodied as software, firmware, hardware or any combination thereof. In one example, monitoring and detection module 170 may, at least in part, be stored or encoded as instructions in memory 152 that are executed by controller 154.

In some examples, programmer 180 may be a handheld device or a microprocessor-based home monitor or bedside programming device. A user, such as a physician, technician, nurse or other clinician, may interact with programmer 180 to communicate with IMD 150. Programmer 180 typically includes a display, a processor, a user interface, and a communication module including wireless telemetry circuitry for communication with IMD 150. For example, a user may interact with programmer 180 via a user interface to retrieve physiological or diagnostic information from IMD 150. A user may also interact with programmer 180 to program IMD 150, e.g., select values for operational parameters of the IMD. A user interacting with programmer 180 may request IMD 10 to perform StO2 and/or THI measurements and transmit results to programmer 180 or request data stored by IMD 150 relating to StO2 monitoring. Programmer 180 receives data from IMD 150 for use in generating data presented on a display including information relating to StO2 monitoring.

Programmer 180 includes a communication module to enable wireless communication with IMD 150 via link 182. Examples of communication techniques used by IMD 150 include low frequency or radiofrequency (RF) telemetry, which may be an RF link established via Bluetooth, WiFi, or MICS. In some examples, programmer 180 may include a programming head that is placed proximate to the IMD 150 to establish and maintain the telemetry link 182, and in other examples programmer 180 and IMD 150 may be configured to communicate using a distance telemetry algorithm and circuitry that does not require the use of a programming head and does not require user intervention to establish and maintain a communication link.

Programmer 180 is used to program calibration coefficients into memory 152 for use by monitoring and detection module 170 or controller 154 in computing absolute StO2 and THI. The programmer 180 is also used to activate IMD 150 to operate sensor 162 to emit light and to acquire a light detector signal during a calibration procedure to enable computation of the calibration coefficients that will be stored in memory 152 or monitoring and detection module 170 for computing absolute StO2 values and calibrated THI measurements. Computation of the calibration coefficients according to the methods described in detail below may be performed by a processor included in programmer 180 or by controller 154. The algorithm and values needed for computing the calibration coefficients may be stored in memory associated with the processor in programmer 180 or programmed into memory 152 for execution by controller 154.

Figure 4:
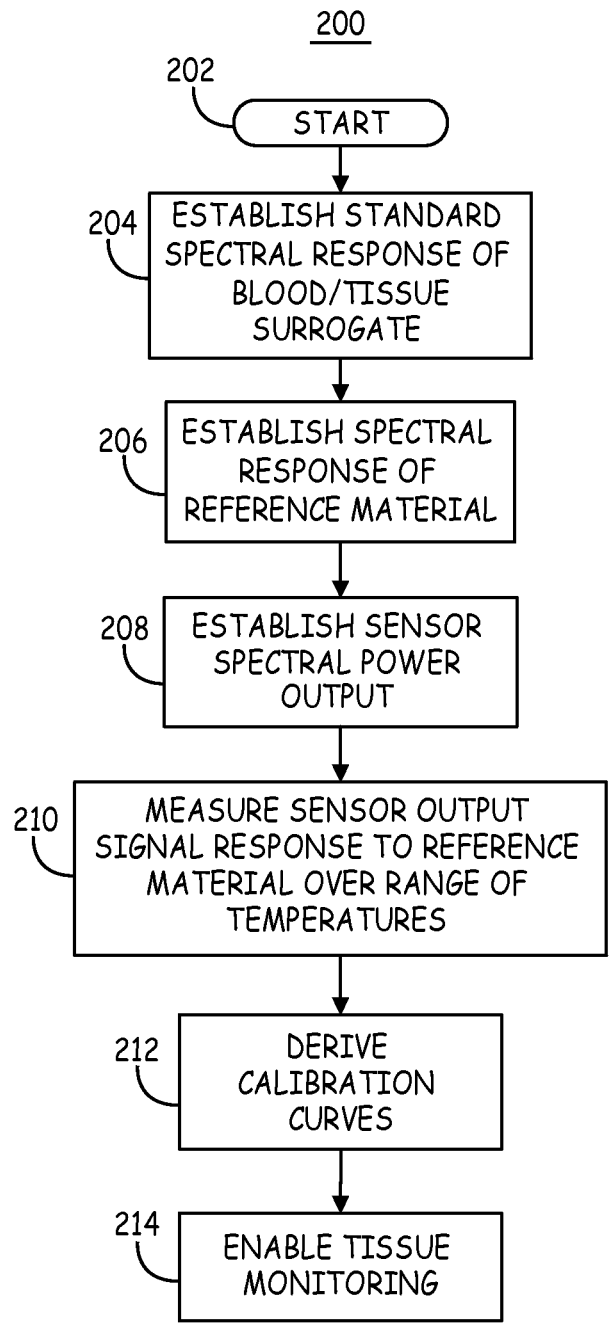
FIG. 4 is a flow chart of a method for calibrating an optical sensor included in a medical device for use in monitoring absolute StO2 according to one embodiment.

FIG. 4 is a flow chart of one method 200 for calibrating an optical sensor included in a medical device for use in monitoring absolute StO2 according to an illustrative embodiment. The calibration procedure is initiated at block 202. The calibration procedure is typically performed during manufacturing of the device such that the device can be programmed with appropriate calibration coefficients prior to implanting or deploying the device for StO2 monitoring. The sensor can be calibrated after assembling the sensor within a medical device, such as IMD 150, or along an elongated medical lead.

At block 204, a standardized spectral response of a composite blood and tissue surrogate is established. The standard spectral response may be taken from published clinical values, but for more accurate calibration of the sensing devices, the standard spectral response is established using a spectrometer that is also used for establishing the standardized spectral response of a reference material and for measuring the spectral output of the optical sensor of each sensing device. The measurement of a standardized spectral response of a composite blood and tissue surrogate will be described in greater detail in conjunction with FIG. 5.

At block 206, the spectral response of a reference material is established, e.g., using the same spectrometer used for establishing the standard spectral response. The reference material is a tissue phantom that is used to correlate a device-specific sensor output signal in response to the reference material to the standard spectral response to the blood/tissue surrogate measured using a spectrometer. In one embodiment, the reference material is a red silicone block though other materials could be used. The reference material is selected to have optical scattering and absorption properties representative of a monitored tissue when the sensor is used in a reflectance mode of operation. These properties may be obtained using materials such as polystyrene or polytetrafluoroethylene combined with an absorptive material such as a dye or hemoglobin.

The standardized spectral responses for a blood/tissue composite and for the reference material are established at blocks 204 and 206 over a full range of light wavelengths that encompass the center light wavelengths measured by the optical sensor. Once these standard spectral responses are established, these operations do not need to be performed again for calibrating every sensor device. Instead, multiple devices such as an entire manufacturing batch or even multiple batches of devices may be calibrated based on the established standard spectral responses according to the methods described below. The spectral responses for the blood/tissue composite and for the reference material may need to be re-established periodically, for example if a new spectrometer is to be employed in the calibration process or upon aging of the reference material that causes a shift or change in the spectral response of the reference material.

At block 208, the spectral power output of the optical sensor is measured using a photometric system, for example using the same spectrometer and an integrating sphere collecting light emitted by the sensor. The spectral power output (Pout) of the sensor may be measured in an oven controlled to body temperature. If a different spectrometer is used than the spectrometer used to establish the standard spectral response and the spectral response to the reference material, error may be introduced in the calibration coefficients but this error may be acceptable depending on the monitoring application.

At block 210, the sensor output signal (light detector signal) response to the reference material is measured. This measurement may be performed over a range of temperatures to enable temperature-dependent calibration of the sensor. The operations performed at blocks 208 and 210 are performed for each manufactured sensing device since each device may have unique light source power spectra and/or light detector response due at least in part to defined specification tolerances. For example, off the shelf emitting and detecting components may vary in power output and light response, respectively, within specification tolerances that are not tightly restricted. This variation will result in device-specific StO2 calibration curves and device specific optical gain. Additional details regarding the methods used to establish the sensor spectral power output and the sensor output signal response to the reference material for each sensing device will be described in conjunction with FIG. 7.

At block 212, calibration curves are derived for each manufactured device to establish and store calibration coefficients for each device. A temperature-dependent optical gain is derived. The optical gain is determined using the standard reference material spectral response and the optical sensor light detector output signal response to the reference material. The optical gain is used to translate the sensor voltage output signal to remittance values that can then be used for computing a light attenuation spectra and subsequently the S2D. The calibration curves derived at block 212 relate the S2D determined from measured attenuation spectra to actual StO2. Remittance mapping between the optical sensor power output and the standard blood spectral response is performed to determine this relationship between StO2 and S2D for each device. An illustrative process for determining the optical gain and deriving the calibration curves will be described in greater detail in conjunction with FIG. 8.

At block 214, the sensing device is enabled for acquiring absolute StO2 measurements for tissue monitoring. The device-specific optical gain and calibration curves (i.e. coefficients and equations defining the curves or corresponding look-up tables) are programmed into each respective sensing device. Tissue monitoring methods using the optical gain and calibration curves derived for a specific device will be described in greater detail in conjunction with FIG. 9.

Figure 5:
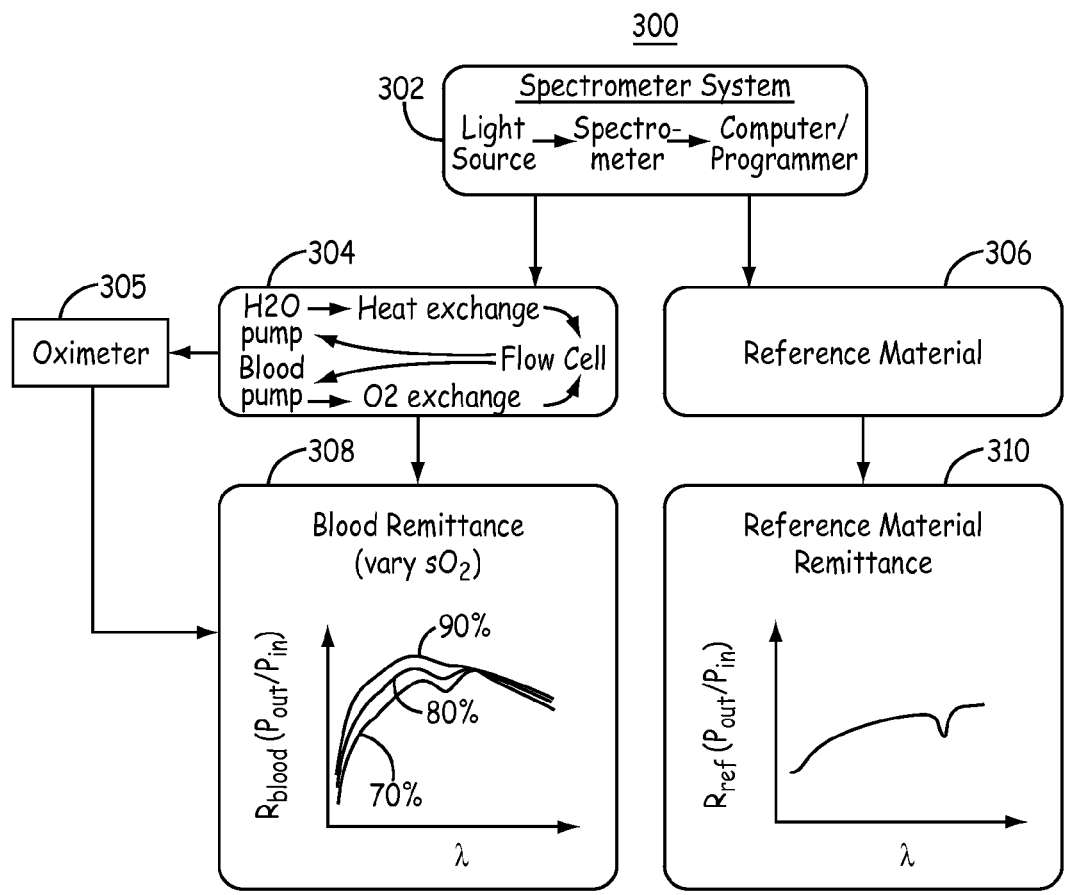
FIG. 5 is a schematic block diagram depicting an apparatus and method for establishing a standard spectral response for blood and a reference material.

FIG. 5 is a schematic block diagram 300 depicting an apparatus and method for establishing the standard spectral response for blood and a reference material. A spectrometer system 302 is used to measure the full spectral response of blood provided in flow loop 304 and the full spectral response of a reference material 306. The spectrometer system 302 generally includes a light source, a spectrometer, and a computer. The light source is provided for illuminating the material to be characterized, in this case blood flowing through a flow cell and mixed or layered with a tissue surrogate in flow loop 304 or a reference material 306. A tissue surrogate is provided in flow loop 304, as described further below, to reflect or scatter light that is not absorbed by blood, enabling measurement of the standard spectral response of blood. As used herein, the "standard spectral response of blood" refers to the spectral response of actual blood that is arranged with a tissue surrogate to enable light not absorbed by the blood to be scattered back to the spectrometer. In this way, light absorption by blood can be measured and the standard spectral response of blood can be established.

Reference material 306 could also be referred to a tissue phantom as it is selected to absorb light at light wavelengths similar to the light absorbance of blood or the tissue to be monitored. In one embodiment the light source is a 150 Watt white light source coupled to an optical fiber positioned to illuminate the material (blood/tissue surrogate composite or reference material) being characterized.

The spectrometer includes a receiving probe for positioning against the material being characterized for receiving light scattered and reflected by the material (i.e. not absorbed by the material). One example of a spectrometer that may be used for establishing the standard spectral responses is the USB4000 Miniature Fiber Optic Spectrometer, available from Ocean Optics, Dunedin, Fla. USA. The received light enters the spectrometer and is reflected off a diffraction grating to separate the light by wavelength. The intensity of the separated wavelengths are measured by a linear detector array. The full spectral response of the blood and the reference block is measured over a range of wavelengths encompassing the wavelengths emitted by the sensor being calibrated. In one embodiment, the spectral response is measured over a range of approximately 600 nm to 1,000 nm in 2 nm increments.

The spectrometer is coupled to a computer or a programmer for receiving the spectral data and generating a spectral response curve. A processor and executable analysis software implemented in the computer or the medical device programmer is used to produce the response curves shown in processing block 308 as remittance (R), defined as the ratio of the spectral power output signal (Pout) to the power in ($P_{in}$), as a function of light wavelength, Λ. The remittance curves defining the standard spectral response data are later used to determine the sensor optical gain and StO2 calibration coefficients.

The flow loop 304 is provided with a flow cell through which blood flows over a tissue surrogate and facilitates positioning of the spectrometer probe and light source for illuminating the blood and tissue surrogate composite and receiving scattered and reflected light. The flow loop 304 will typically include a fluid pump for pumping blood through a gas exchanger that allows the oxygen saturation of the blood to be controlled. The blood pump, gas exchanger and flow cell are fluidly coupled using conduits or tubing to provide a closed loop.

The actual blood oxygen saturation may be measured by an oximeter 305. The oximeter may be coupled to the flow loop 304 to enable StO2 and hemoglobin concentration measurements. Alternatively, periodic blood draws may be taken from the flow loop to obtain actual oxygen saturation and hemoglobin concentration measurements. The oximeter 305 may be coupled to the computer or programmer receiving the spectrometer data to provide input to the processing block 308. The actual blood StO2 measurements can be combined with the spectrometer data for generating multiple remittance curves corresponding to multiple blood oxygen saturation levels. In one embodiment, StO2 is varied between 0% and 100% in desired increments. The increments for varying StO2 may be approximately 1%, 3%, 5% or any other selected increment for providing a desired resolution and accuracy of the calibration curves.

The flow loop 304 is shown to additionally include a water pump separately coupled to a heat exchanger and the flow cell for pumping temperature-controlled water through separate conduits within the flow cell but adjacent the flowing blood for controlling the blood temperature. Temperature may be controlled at approximately body temperature. One embodiment of a fixture used for the flow cell and including separate blood flow and water flow conduits is shown in FIG. 6, described below.

Processing block 308, which may be implemented in a computer or programmer, generates remittance data from the received the spectrometer output and oximeter readings. Remittance curves are generated by plotting remittance (Pout/Pin) as a function of light wavelength for each oxygen saturation. The remittance curves may be provided with a wavelength resolution of approximately 1 to 2 nm or other desired resolution. Three example remittance curves for StO2 of 70%, 80% and 90% are shown, however, it is contemplated that at least twenty-five or more remittance curves would be obtained when StO2 is varied between 0 and 100%. In this way, the expected remittance measurement at a given wavelength for a given blood oxygen saturation at body temperature is established in the standard blood response remittance curves.

The spectrometer system 302 is additionally used to generate remittance data 310 for the reference material 306. The reference material 306 or tissue phantom is used as a "blood/tissue model" and is illuminated by the spectrometer light source and the spectrometer probe is positioned to receive light reflected and scattered by material 306. The remittance curve processing block 310 establishes the expected remittance to be measured for the reference material at wavelengths encompassing the range of wavelengths emitted and measured by the sensor being calibrated.

Figure 6:
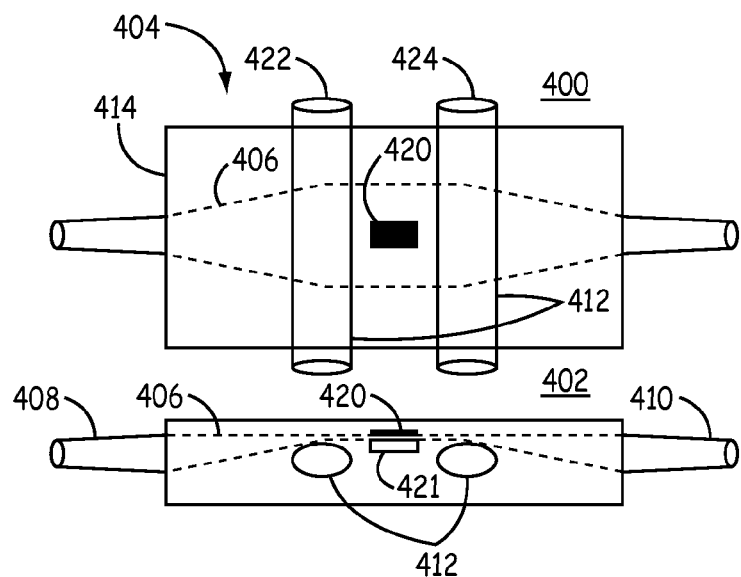
FIG. 6 is a top plan view and side view of a flow cell that may be used in a blood flow loop for establishing a standard spectral response of blood.

FIG. 6 is a top plan view 400 and side view 402 of a flow cell 404 that may be used in flow loop 304 for establishing the spectral response of actual blood arranged in a composite with a tissue surrogate. A flow cell fixture 414 is formed of a transparent material and includes a blood flow conduit 406 extending through fixture 414 and terminating at proximal and distal fluid couplings 408 and 410 for connecting tubes or hosing to establish fluid communication with the blood pump. The spectrometer probe 420 is positioned along the blood flow conduit 406. Below the blood flow conduit 406 is a tissue surrogate material 421, as seen in side view 402. The tissue surrogate material is selected to have very low absorption properties and high scattering properties. In this way, light that is not absorbed by the blood is scattered or reflected back to the spectrometer probe, thereby allowing the blood spectral response to be measured. In the embodiment shown, the blood flowing through conduit 406 and tissue surrogate 421 are arranged in a layered configuration. The tissue surrogate is provided as Plastazote LD45 low density polyethylene foam. In other embodiments, the blood and tissue surrogate material could be mixed or arranged in other configurations to provide a model of the scattering or reflection by tissue of light not absorbed by actual blood.

One or more water flow conduits 412 extend through the fixture 414 and terminate in respective fluid couplings 422 and 424 for connecting in fluid communication with the water pump. The water conduits 412 provide temperature controlled water flowing adjacent the blood conduit 406 in the vicinity of the spectrometer probe 420 to maintain the blood at a controlled temperature.

Figure 7:
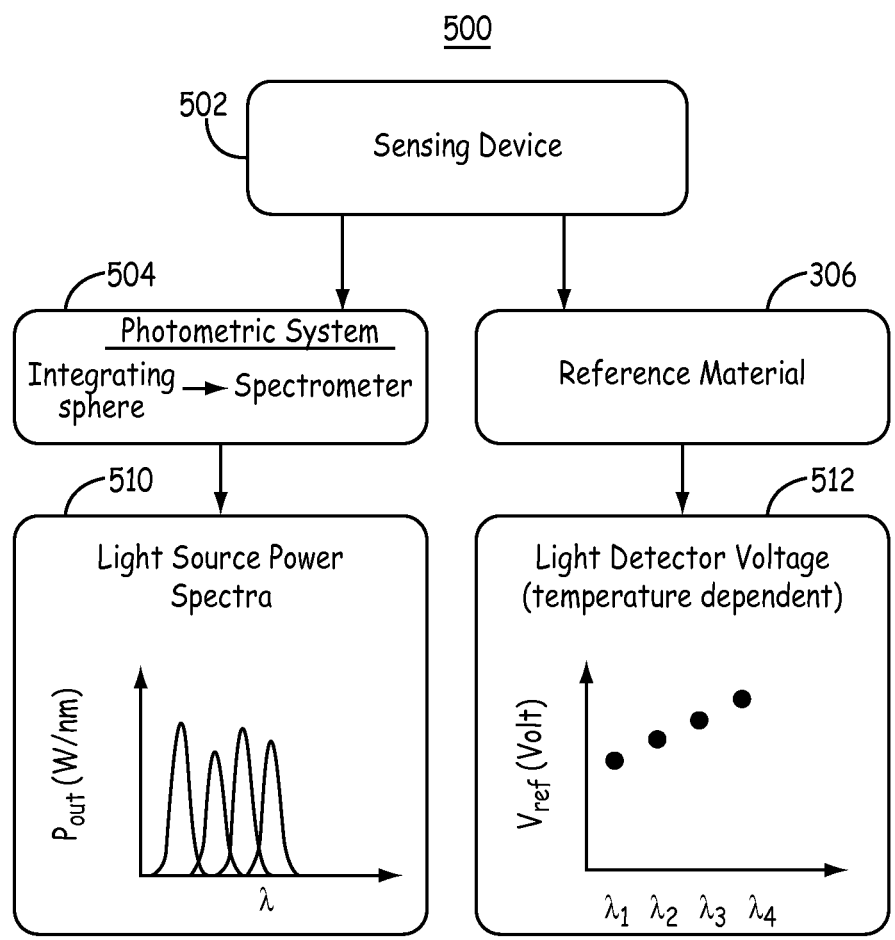
FIG. 7 is a schematic block diagram depicting an apparatus and associated method for establishing power output spectra of the optical sensor being calibrated and the light detector voltage signal produced in response to the reference material.

FIG. 7 is a schematic block diagram 500 depicting apparatus and an associated method for establishing power output spectra of the optical sensor being calibrated and the light detector voltage signal produced in response to the reference material 306. The sensing device 502, which includes the optical sensor being calibrated, is enabled to emit and detect light during the calibration procedure, for example in response to a user command delivered via a programmer and wireless telemetry.

During light emission by the optical sensor, the emitted light is collected by a photometric system 504 used to measure the optical power of the emitted light. The photometric system includes an integrating sphere for collecting the emitted light and a spectrometer for measuring the power in Watt/nm. The spectrometer included in photometric system 504 is the same spectrometer used to establish the standard spectral response of blood in one embodiment in order to eliminate or minimize measurement error that may occur between photometric systems.

The spectrometer output is received by processing block 510, which may be implemented in a computer or programmer processor, for establishing the Pout spectra for each of the light sources included in the optical sensor. Four wavelengths are shown in the example Pout vs. λ curves corresponding to each of four LEDs included in an optical sensor according to one embodiment.

The sensing device 502 is additionally used to measure the light detector voltage for each of the emitted wavelengths when the sensing device 502 is positioned against the block of reference material 306. The light detector voltage signal is measured or plotted for each wavelength by processing block 512 for use with the standard spectral response for the reference material to translate the measured optical sensor output voltage to remittance. In other words, the optical gain of the particular optical sensor for converting a voltage signal to a remittance measurement can be computed using the standard remittance curve for the reference material as measured by the spectrometer and the voltage signal generated by the optical sensor when positioned against the same reference material 306.

The light detector voltage is measured for multiple controlled temperature settings by positioning the reference material and sensing device in an oven. Thus, the light source voltage output for each of the emitted light wavelengths, e.g. $\lambda_1$ through $\lambda_4$, is measured at multiple temperatures settings, e.g. 10 temperature settings encompassing a range of temperatures expected to be encountered during normal device operation in or on a patient's body. The four plotted voltage signal points shown in processing block 512 for four respective wavelengths represent the light detector voltage signal recorded at one temperature at each wavelength.

The Pout data determined at processing block 510 is used with the standard blood remittance curves (block 308, FIG. 5) to derive the device-specific calibration curves relating remittance to wavelength. The light source power spectra data determined at processing block 510 and the light detector voltage response determined at block 512 are stored in memory associated with the processor that will perform the calibration curve and optical gain calculations as described next in conjunction with FIG. 8.

Figure 8:
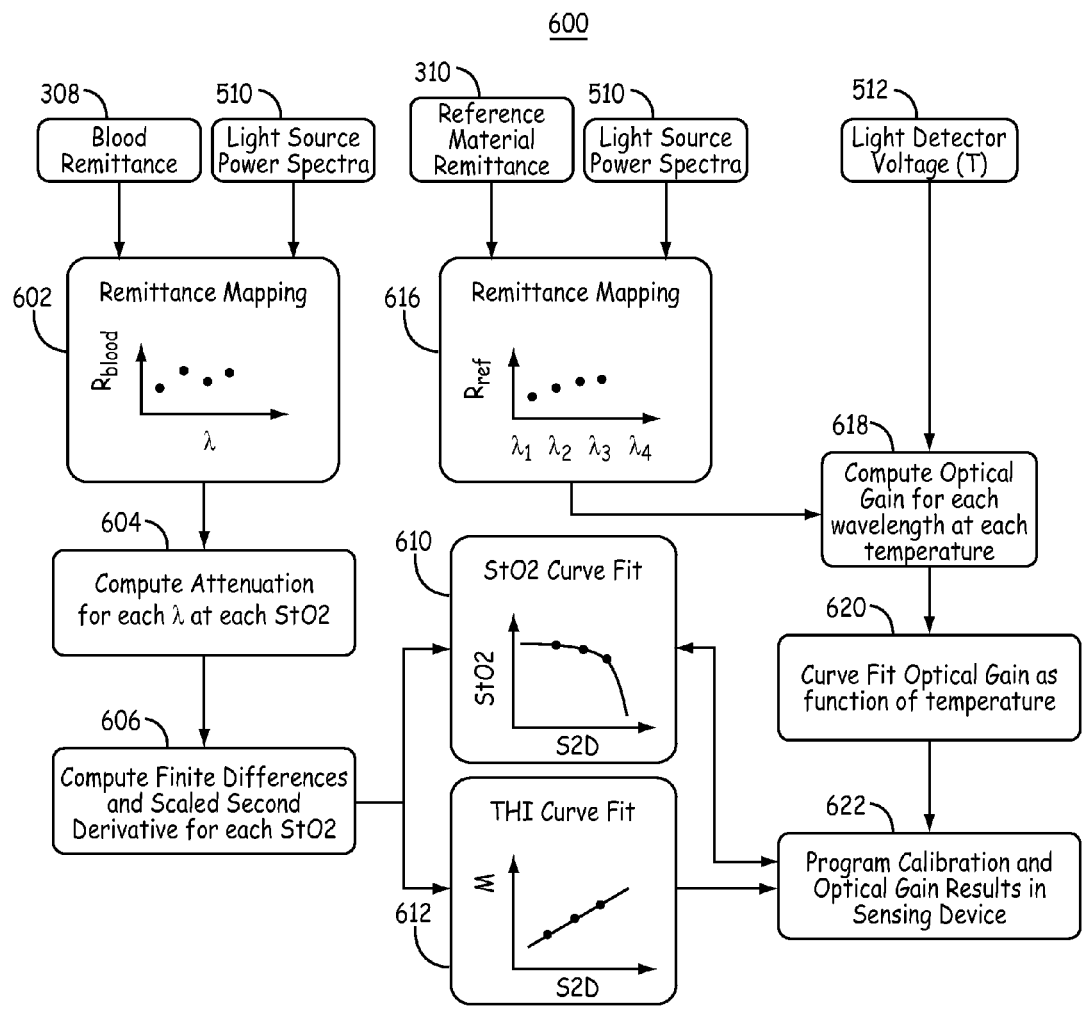
FIG. 8 is a flow chart of a method for deriving device-specific calibration coefficients and optical gain for an optical sensing device according to one embodiment.

FIG. 8 is a flow chart 600 of a method for deriving optical sensor specific calibration coefficients and optical gain according to one embodiment. The calibration method shown by flow chart 600 is performed for each manufactured device using the established standard blood remittance data produced and stored at processing block 308 and established standard reference material remittance data produced and stored at processing block 310 as described in conjunction with FIG. 5. Device-specific calibration values are determined using the standard remittance data and the device specific light source power spectra produced and stored at processing block 510 and light detector voltage data produced and stored at processing block 512 as described in conjunction with FIG. 7.

The calibration method operations presented in conjunction with FIG. 8 may be performed by a processor included in the sensing device or in a processor in a programmer or computer with the results of the calibration method programmed into the sensing device to enable tissue monitoring using absolute StO2 measurements.

At block 602, remittance mapping is performed using the standard blood remittance data from processing block 308 and the measured light source power spectra data from processing block 510 as input. The remittance mapping is performed by determining, for a given StO2, the remittance of blood at each of the light source wavelengths, e.g. 4 LED wavelengths, as a weighted average computed as the dot product of the blood remittance curve and the light source power spectra curve divided by the summation of the light source power spectra curve data points for each emitted wavelength. Mathematically, the weighted average remittance of blood at a given StO2 ($\overline{R(\lambda_n)_{blood}}$) can be computed for each emitted center wavelength $\lambda_n$, using the following equation:

$$\overline{R(\lambda_n)_{blood}} = \frac{\sum_{i=1}^{j} R^i_{blood} \times P^i_{out}}{\sum_{i=1}^{j} P^i_{out}}$$

wherein $R^i_{blood}$ represents remittance at each incremental wavelength i measured by the spectrometer. $P^i_{out}$ represents Pout measured by the sepectrometer at each incremental wavelength i during activation of the $\lambda_n$ light source of the sensing device. Expressed in other words, in the numerator of the above equation, the products of the standard blood remittance and the output power of the sensing device light at each wavelength i are summed over all wavelengths i=1 to j in the range of the standard blood spectral response curve. The blood spectral response curve may be measured over a range of wavelengths i of 600 nm to 1000 nm in 2 nm increments in one embodiment. The numerator is divided by the summation of Pout measured over the spectrometer measurement wavelength range, i=1 to j, during light emission by the $\lambda_n$ light source.

This process for computing ($\overline{R(\lambda_n)_{blood}}$) is repeated to obtain ($\overline{R(\lambda_n)_{blood}}$) for each center wavelength emitted by the sensing device. For example, for each LED emitting light at 680, 720, 760 and 800 nm, a respective $R(680)_{blood}$, $R(720)_{blood}$, $R(760)_{blood}$ and $R(800)_{blood}$ is computed using the above equation. This remittance mapping performed for each $\lambda_n$ light source is performed for each StO2 and will thus produce four remittance values (one for each light source wavelength) for each StO2 blood remittance curve as shown in processing block 602.

For each weighted average remittance value, light attenuation is computed at block 604 as the negative natural logarithm of the weighted average remittance (A=−ln(R)). The attenuation computation yields the attenuation at each of the four discreet wavelengths emitted by the sensor light sources that would be expected to be measured by the optical sensor for a given StO2. The attenuation spectrum corresponding to the four emitted wavelengths is determined for each blood spectral response curve obtained for the varying StO2.

At block 606, finite differences between the computed attenuation values at each wavelength for a given StO2 are computed to estimate the first derivatives of the attenuation spectra. For example, if the sensing device includes LEDs emitting light at 680 nm, 720 nm, 760 nm, and 800 nm, the approximation of the first derivatives of the attenuation spectra at 700 nm, 740 nm and 780 nm are, respectively:

$$d700 = (A_{720} - A_{680})/40$$

$$d740 = (A_{760} - A_{720})/40$$

$$d780 = (A_{800} - A_{760})/40$$

or more generally as:

$$d\{(\lambda_{n+1} + \lambda_n)/2\} = (A_{n+1} - A_n)/(\lambda_{n+1} - \lambda_n).$$

The second derivatives of the attenuation spectra are then estimated using finite differences of the first derivatives or:

$$D720 = (d740 - d700)/\Delta\lambda$$

$$D760 = (d780 - d740)/\Delta\lambda$$

The scaled second derivative (S2D) at 720 nm is the ratio of D720/D760. This S2D is correlated to StO2 and is computed for each StO2 attenuation spectra determined at block 606 from the weighted average remittances.

At block 610 the known StO2 and computed S2D(720) for each StO2 blood remittance curve are plotted and curve fitting techniques are used to derive an equation defining the S2D vs. StO2 curve. In one embodiment, the equation defining StO2 as a function of S2D(720) is given by:

$$StO2 = Ae^{B*S2D(720)} + C*S2D(720) + D.$$

The coefficients A, B, C and D are solved for using curve fitting techniques and these coefficients are programmed into the memory of the sensing device at block 622

If the sensing device is configured to monitor THI, a curve fitting technique is applied at processing block 612 to the approximated second derivative at 760 nm (D760) of the attenuation spectra for each hemoglobin concentration measured during acquisition of the blood remittance curves. THI may be given by the equation THI=−m*D760 wherein m is computed as a function of S2D(720) using a curve fitting technique applied to the measured THI and computed D(760) and S2D(720) values. During the duration of test, the actual hemoglobin concentration may be measured and recorded and used in a regression solution for the slope term m. The slope term m may be stored as a look-up table of values corresponding to respective S2D(720) values in the sensing device or as a best fit equation defining m as a function of S2D(720), which may be a linear function.

In addition to determining the calibration curves for StO2 and THI at blocks 610 and 612, the optical gain of the sensing device is determined at block 618 using the standard reference material remittance curve from processing block 310, the sensing device light source power output data from processing block 510, and the sensing device light detector voltage signal response to the reference material from processing block 512.

At block 616, remittance mapping is performed using the established reference material remittance curve 310 measured by the spectrometer and the device-specific light source power spectra 510. The weighted average remittance, $R(\lambda_n)_{reference}$, for the reference material is computed for each of the emitted wavelengths of the sensor, $\lambda_n$. The weighted average remittance corresponding to the wavelength $\lambda_n$ of a given light source is computed as the dot product of the measured remittance curve for the reference material and the measured Pout curve for a given light source over the measured wavelength range i=1 to m, to obtain a weighted average reference material remittance at each of the discreet wavelengths emitted by the optical sensor. This remittance mapping provides an expected remittance that would be measured for the reference material at the wavelengths emitted by the sensing device.

At block 618, this weighted average remittance at each wavelength $\lambda_n$ is divided by the light detector voltage signal measured at the same wavelength to compute the optical gain, f, of the sensing device at each wavelength $\lambda_n$. If the light detector voltage signal response to the reference material was performed for multiple temperature measurements, the relationship between the computed optical gain for a given wavelength, $f_A$, and the measured temperature sensor voltage is determined at block 620. For example, for a given wavelength, the computed $f_A$ for varying measured temperatures is used to solve for the coefficients A, B and C in the equation $$f_A = A + BVtemp + CVtemp^2,$$

wherein Vtemp is the temperature sensor voltage.

The optical gain for each wavelength $\lambda_n$ emitted by the sensing device may then be stored as a look-up table of values based on measured temperature or the computed coefficients A, B and C in the above optical gain equation may be programmed into the sensing device at block 622. The optical gain values are programmed in the sensing device for use during tissue monitoring.

Figure 9:
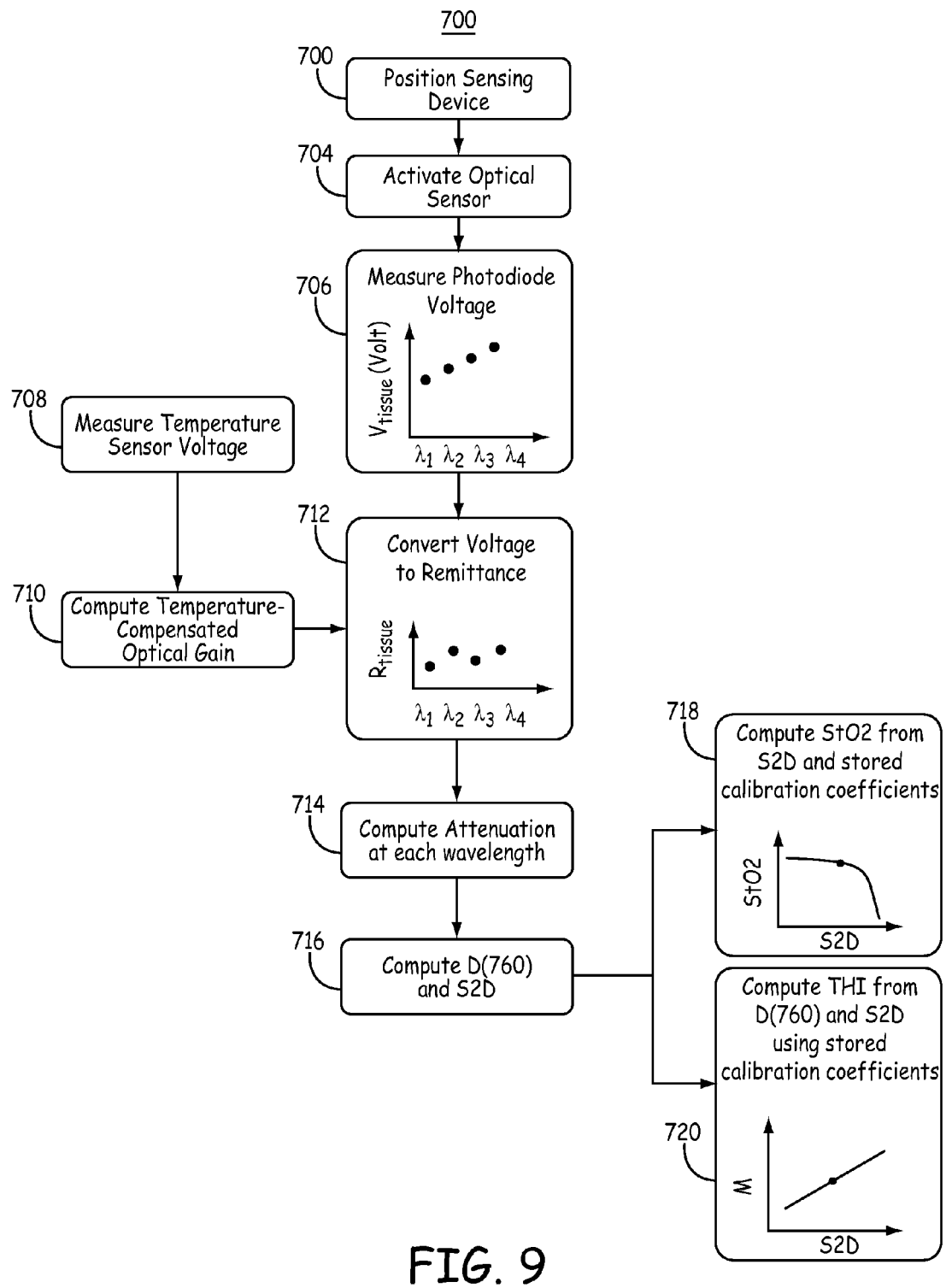
FIG. 9 is a flow chart of one method for monitoring absolute StO2 and a calibrated total hemoglobin concentration index (THI) in a patient using an optical sensor calibrated using the methods described herein.

FIG. 9 is a flow chart 700 of a method for monitoring absolute StO2 and calibrated THI in a patient using an optical sensor included in a medical device and has been calibrated using the methods described above. At block 702, the sensing device is implanted or positioned at a desired sensing site, such that the emitting and detecting portions of the sensor are operationally positioned against a targeted tissue volume. At block 704, the optical sensor is activated by sensor control circuitry to emit light and the light detector signal is collected in accordance with any desired tissue StO2 monitoring protocol. The light detector voltage signal is measured at block 706 at each of the four wavelengths emitted by the emitting portion. As shown in block 706, the light detector is embodied as a photodiode in one embodiment and produces a voltage signal which is processed to determine the voltage corresponding to four wavelengths of light emitted by 4LEDs.

At the time of light detector signal collection, a temperature sensor voltage signal is also acquired at block 708. The temperature sensor voltage (Vtemp) is used to compute a temperature-compensated optical gain at block 710, using the optical gain calibration coefficients established during the method described in conjunction with FIG. 8 and stored in the sensing device memory. The temperature-compensated optical gain, $f_{\lambda,n}$, is computed for each wavelength n emitted by the sensing device, e.g. $f_{\lambda,n} = A + BVtemp + CVtemp^2$ using stored coefficients A, B and C. Alternatively, for a given temperature sensor voltage, the corresponding optical gain for each wavelength can be determined from a look-up table stored in the sensing device memory.

At block 712, processing circuitry of the sensing device converts the light detector voltage measured at each emitted wavelength to a remittance value. The light detector voltage is converted to remittance by multiplying by the temperature-compensated optical gain ($R_{\lambda,n\ tissue} = f_{\lambda,n} \times V_{\lambda,n}$). The remittance value is converted at block 714 to an attenuation measurement at each wavelength $\lambda_n$ by determining the negative natural logarithm of each remittance $R_{\lambda,n\ tissue}$, i.e., $A_{\lambda,n} = -\ln\{R_{\lambda,n}\}$.

At block 716, the finite differences of the attenuation measurements at each wavelength $\lambda_n$ are used to determine second derivates of the attenuation measurements and S2D(720) used for computing StO2. In one embodiment the S2D at 720 nm is computed by determining the ratio of the second derivative at 720 nm (D720) and the second derivative at 760 nm (D760) as described above. Knowing S2D(720), the stored StO2 calibration curve coefficients (from processing block 610) are used to compute a calibrated measurement of StO2 at bock 718.

Additionally, a calibrated THI can be computed at block 720. The slope term m for computing THI is determined using the computed S2D(720) and stored calibration coefficients defining a linear relationship between m and S2D (from processing block 612). THI is computed as the product of the S2D-dependent M and D760. The computed values of StO2 and THI produced at blocks 718 and 720 may then be used by the sensing medical device according to a monitoring protocol for detecting a physiological event or condition. For example, the StO2 and THI measurements may be averaged with other StO2 and THI measurements, compared to a detection threshold, or used in combination with other physiological measurements in a detection algorithm. The StO2 and THI measurements may be used in controlling patient or clinician alerts and/or controlling a device-delivered therapy. Additionally or alternatively, the StO2 and THI data may be stored for later transmission and display to a clinician for use in patient diagnosis or therapy management.

Thus, a medical device having an optical sensor and an associated calibration and tissue monitoring method have been presented in the foregoing description with reference to specific embodiments. It is appreciated that various modifications to the referenced embodiments may be made without departing from the scope of the disclosure as set forth in the following claims.

The invention claimed is:

1. A method for using a medical device comprising an optical sensor to measure calibrated oxygen saturation in a body tissue, the method comprising:

establishing a standard spectral response of blood for a plurality of oxygen saturations by a control processor coupled with the optical sensor;

establishing a standard spectral response of a reference material by a spectrometer;

determining a spectral power output of each wavelength emitted by the optical sensor by the spectrometer;

obtaining an optical sensor output signal response of each wavelength to the reference material by a detector of the optical sensor;

determining a calibration curve for the optical sensor using the measured spectral power output and the standard spectral response of blood by the control processor;

determining an optical gain for each wavelength for converting a voltage signal generated by the optical sensor to a remittance measurement by the control processor, the optical gain being determined by:

using the standard spectral response of the reference material and the measured spectral power output of the optical sensor to generate a remittance measurement value for the reference material that is expected to be measured by the optical sensor, wherein generating the remittance

17 measurement value for the reference material comprises computing a dot product of the standard spectral response of the reference material and the spectral power output of each wavelength emitted by the optical sensor, and dividing the expected remittance measurement value by an actual voltage signal produced by the optical sensor responsive to the optical sensor detecting remitted light at a corresponding wavelength from the reference material; and storing the calibration curve and the optical gain.

2. The method of claim 1, wherein the optical sensor comprises a plurality of light sources emitting light at spaced apart wavelengths, and wherein establishing the spectral response of blood comprises establishing the spectral response over a range of light wavelengths encompassing the spaced apart wavelengths.

3. The method of claim 1, further comprising measuring the optical sensor output signal response to the reference material at a plurality of temperatures and determining an optical gain for each of the plurality of temperatures.

4. The method of claim 3, further comprising determining a temperature compensated optical gain curve for each of a plurality of spaced apart wavelengths emitted by the optical sensor, and storing the temperature-compensated optical gain curve for each of the wavelengths.

5. The method of claim 1, wherein computing the calibration curve for the optical sensor comprises computing a weighted average remittance at each of a plurality of wavelengths emitted by the optical sensor for each of the plurality of oxygen saturations using the standard spectral response of blood and the measured spectral power output.

6. The method of claim 5, wherein computing the calibration curve comprises converting the weighted average remittances for each of the plurality of oxygen saturations to an attenuation spectrum.

7. The method of claim 6, wherein computing the calibration curve further comprises determining a scaled second derivative of the attenuation spectra for each of the plurality of oxygen saturations.

8. The method of claim 7, wherein computing the calibration curve comprises determining calibration coefficients for a curve defining the plurality of oxygen saturations as a function of the scaled second derivative.

9. The method of claim 7, further comprising computing a calibration coefficient for computing a total hemoglobin concentration index as a function of a second derivative of the attenuation spectra and the scaled second derivative.

10. The method of claim 1, further comprising computing the oxygen saturation in a tissue by measuring a voltage signal of the optical sensor, applying the stored optical gain to convert the voltage signal to a remittance signal, converting the remittance signal to an attenuation signal, computing a scaled second derivative of the attenuation signal, and computing an absolute oxygen saturation of the tissue using the scaled second derivative and the stored calibration curve.

11. The method of claim 1, further comprising:
establishing the standard spectral response of blood and the standard spectral response of the reference material using a common spectrometer a single time;
determining a device-specific spectral power output for each of a plurality of optical sensors;
determining a device-specific calibration curve for each of the plurality of optical sensors using the single standard spectral response of blood and the respective device-specific spectral power outputs; and

18 computing a device-specific optical gain for each of the plurality of optical sensors by using the single standard spectral response of the reference material and the respective device-specific spectral power outputs to generate an expected remittance curve for the reference material for each of the plurality of optical sensors and dividing the expected remittance curves by respective actual voltage signals produced by respective ones of the plurality of optical sensors responsive to detecting remitted light from the reference material.

12. The method of claim 11, further comprising:
programming the device-specific calibration curve and the device specific optical gain into an implantable sensing device comprising a respective one of the plurality of optical sensors; and
enabling processing circuitry of the implantable sensing device to convert an optical sensor voltage signal to a measured remittance using the programmed device-specific optical gain.

13. The method of claim 1, wherein determining the spectral power output of the optical sensor comprises collecting light emitted by the optical sensor and measuring the collected light using the spectrometer.

14. A medical device system for measuring absolute oxygen saturation in a body tissue, the system comprising:
an optical sensor;
a memory storing a standard spectral response of blood for a plurality of oxygen saturations using a spectrometer and a standard spectral response of a reference material;
a control processor coupled with the optical sensor and the memory, the processor configured to:
cause to the optical sensor to emit light at spaced apart wavelengths by a plurality of light sources to enable measuring the spectral power output of the optical sensor, acquire the optical sensor output signal response of each wavelength to the reference material by a detector of the optical sensor, compute a calibration curve for the optical sensor using the measured spectral power output and the standard spectral response of blood, and
compute an optical gain for each wavelength by:
using the standard spectral response of the reference material and the measured spectral power output of the optical sensor to generate a remittance measurement value for the reference material that is expected to be measured by the optical sensor, wherein the remittance measurement value is generated by computing a dot product of the standard spectral response of the reference material and the spectral power output of each wavelength emitted by the optical sensor, and
dividing the expected remittance measurement value by an actual voltage signal produced by the optical sensor responsive to the optical sensor detecting remitted light at a corresponding wavelength from the reference material; and
a sensor memory coupled to the optical sensor to store the computed calibration curve and the optical gain.

15. The system of claim 14, wherein the standard spectral response of blood comprises the spectral response over a range of light wavelengths encompassing the spaced apart wavelengths.

16. The system of claim 14, wherein the processor receives the optical sensor output signal response to the reference material at a plurality of temperatures and is configured to determine an optical gain for each of the plurality of temperatures.

17. The system of claim 16, wherein the processor is further configured to determine a temperature compensated optical gain curve for each of a plurality of spaced apart wavelengths emitted by the optical sensor, and the sensor memory is programmed to store the temperature-compensated optical gain curve for each of the wavelengths.

18. The system of claim 14, wherein computing the calibration curve for the optical sensor comprises computing a weighted average remittance at each of a plurality of wavelengths emitted by the optical sensor for each of the plurality of oxygen saturations using the standard spectral response of blood and the measured spectral power output.

19. The system of claim 18, wherein computing the calibration curve comprises converting the weighted average remittances for each of the plurality of oxygen saturations to an attenuation spectrum.

20. The system of claim 19, wherein computing the calibration curve further comprises determining a scaled second derivative of the attenuation spectra for each of the plurality of oxygen saturations.

21. The system of claim 20, wherein computing the calibration curve comprises determining calibration coefficients for a curve defining the plurality of oxygen saturations as a function of the scaled second derivative.

22. The system of claim 20, wherein the processor is further configured to compute a calibration coefficient for computing a total hemoglobin concentration index as a function of a second derivative of the attenuation spectra and the scaled second derivative.

23. The system of claim 14, wherein the oxygen saturation in a tissue is determined by obtaining a voltage signal of the optical sensor, applying the stored optical gain to convert the voltage signal to a remittance signal, converting the remittance signal to an attenuation signal, computing a scaled second derivative of the attenuation signal, and computing an absolute oxygen saturation of the tissue using the scaled second derivative and the stored calibration curve.

* * * * *